United States Patent [19]
Yadav

[11] Patent Number: 6,077,992
[45] Date of Patent: Jun. 20, 2000

[54] BINARY VIRAL EXPRESSION SYSTEM IN PLANTS

[75] Inventor: Narendra S. Yadav, Chadds Ford, Pa.

[73] Assignee: E. I. du Pont de Nemours and Company, Wilmington, Del.

[21] Appl. No.: 09/178,089

[22] Filed: Oct. 23, 1998

Related U.S. Application Data

[60] Provisional application No. 60/063,504, Oct. 24, 1997.

[51] Int. Cl.[7] .......................... C12N 15/82; C12N 15/90; A01H 5/00; A01H 5/10
[52] U.S. Cl. .................... 800/278; 435/69.1; 435/320.1; 435/468; 800/285; 800/287; 800/288; 800/298; 800/300; 800/302
[58] Field of Search ............................... 435/69.1, 320.1, 435/410, 419, 468; 536/24.1, 23.72; 800/278, 280, 287, 288, 295, 298, 285, 302

[56] References Cited

U.S. PATENT DOCUMENTS 4,855,237  8/1989  Morinaga et al. .................... 536/23.72

FOREIGN PATENT DOCUMENTS

| | | |
|---|---|---|
| 221044 | of 0000 | European Pat. Off. ......... C12N 15/00 |
| 0 425 004 | 5/1991 | European Pat. Off. ......... C12N 15/40 |
| WO 9534668 | of 0000 | WIPO ............................. C12N 15/83 |
| WO 9836083 | of 0000 | WIPO . |
| WO 94 19477 | 9/1994 | WIPO ............................. C12N 15/82 |

OTHER PUBLICATIONS

Aryan et al, Mol. Gen. Genet., vol. 225, pp. 65–71, 1991
Vgacki et al, Nucl. Acids Res., vol. 19, pp. 371–377, 1991.
Topfer et al, Plant Cell, vol. 1, pp. 133–139, 1989.
Timmermans et al, Annu Rev. Plant Physiol. Mol. Biol., vol. 45, pp. 79–112, 1994.
Hennig et al, Plant J., vol.1 4, pp. 481–483, 1993.
Jach et al, Plant J., vol. 8, pp. 97–109, 1995.
Blockland et al, Plant J., vol. 6, pp. 861–877, 1994.
Hong et al., Resistance to geminivirus infection by virus--induced expression of dianthin in transgenic plants., *Virology*, (Jun. 1, 1996 220 (1) 119–27).
Hong et al., "Transactivation of dianthin transgene by African cassava mosaic virus AC2.", *Virology*, (Feb. 17, 1997 118 (2) 383–7).
Sablowski et al., *Proc. Natl. Acad. Sci.* USA, 92, 6901–6905, 1995.
Hayes et al., *Nucleic Acids Res.*, 17, 2391–2403, 1989.
Hayes et al., *Nature* (London), 334, 179–182, 1988.
Rogers et al., *Cell*, 45, 593–600, 1986.
Goodman, *J. Gen. Virol.*, 54, 9–21, 1981.
Hanley–Bowdoin et al., *Plant Cell*, 1, 1057–1067, 1989.
Hanley–Bowdoin et al., *Proc. Natl. Acad. Sci.* U.S.A., 87, 1446–1450, 1990.
Hayes et al., *Nucleic Acids Res.*, 17, 10213–10222, 1989.
Al–Kaff et al., *Science* (Washington, DC), 279, 2113–2115, 1998.
Needham et al., *Plant Cell Rep.*, 17, 631–639, 1998.
Senior et al., *Biotechnol. Genet. Eng. Rev.*, 15, 79–119, 1998.
Thomas et al., *Plant Growth Regul.*, 25, 205, 1998 abstracts.
Ruiz et al., *Plant Cell*, 10, 937–946, 1998.
Kjemtrup et al., *Plant J.*, 14, 91–100, 1998.
Atkinson et al., *Plant J.*, 15, 593–604.

*Primary Examiner*—Elizabeth F. McElwain
*Assistant Examiner*—Ashwin D. Mehta

[57] ABSTRACT

This invention relates to a regulated binary plant viral expression system. It is comprised of two chromosomally-integrated components. One component is a proreplicon, which contains cis-acting viral sequences required for replication and a contains a target gene. The other component is a chimeric trans-acting replication gene comprising a regulated promoter operably-linked to the coding region for a viral replication protein. The proreplicon lacks the replication gene essential for replicon replication, and thus cannot undergo autonomous episomal replication. However, regulated expression of the trans-acting replication protein in plant cells also containing the proreplicon will trigger the release of free replicon from the integrated proreplicon, result in its episomal replication in trans, and result in the expression of the target gene, if present, through gene amplification. The expression system is useful for both production of foreign proteins as well as silencing endogenous genes and transgenes in plant tissue. Tissue-specific expression is controlled by the choice of promoter controlling the transcription of the trans-acting replication gene.

22 Claims, 1 Drawing Sheet

BINARY VIRAL EXPRESSION SYSTEM IN PLANTS

This application claims benefit of Provisional Application Ser. No. 60/063,504 filed Oct. 24, 1997 and of Provisional Application No. unknown filed Sep. 23, 1998.

FIELD OF INVENTION

The present invention relates to the field of molecular biology and the genetic transformation of plants with foreign gene fragments. More particularly, this invention relates to a heritable plant viral expression system useful for expressing transgenes in plants.

BACKGROUND OF THE INVENTION

Plant transgenic work is beset with low and inconsistent levels of transgene expression. Episomal vectors are expected to overcome these problems. In microbes, episomal (plasmid) vectors are possible because these vectors can be maintained by selection. Although plant viruses have been used as episomal expression vectors, their use has been restricted to transient expression because of lack of selection and/or their cellular toxicity (U.S. Pat. No. 4,855,237, WO 9534668).

Plant viruses

Viruses are infectious agents with relatively simple organization and unique modes of replication. A given plant virus may contain either RNA or DNA, which may be either single- or double-stranded.

Rice dwarf virus (RDV) and wound tumor virus (WTV) are examples of double-stranded RNA plant viruses. Single-stranded RNA plant viruses include tobacco mosaic virus (TMV), turnip yellow mosaic virus (TYMV), rice necrosis virus (RNV) and brome mosaic virus (BMV). The RNA in single-stranded RNA viruses may be either a plus (+) or a minus (−) strand. Although many plant viruses have RNA genomes, organization of genetic information differs between groups. The genome of most monopartite plant RNA viruses is a single-stranded molecule of (+)-sense. There are at least 11 major groups of viruses with this type of genome. An example of this type of virus is TMV. At least six major groups of plant RNA viruses have a bipartite genome. In these, the genome usually consists of two distinct (+)-sense single-stranded RNA molecules encapsidated in separate particles. Both RNAs are required for infectivity. Cowpea mosaic virus (CPMW) is one example of a bipartite plant virus. A third major group, containing at least six major types of plant viruses, is tripartite, with three (+)-sense single-stranded RNA molecules. Each strand is separately encapsidated, and all three are required for infectivity. An example of a tripartite plant virus is alfalfa mosaic virus (AMV). Many plant viruses also have smaller subgenomic mRNAs that are synthesized to amplify a specific gene product. Plant viruses with double-stranded DNA genome include Cauliflower Mosaic virus (CaMV).

Geminiviruses

Plant viruses with single-stranded DNA genomes are represented by geminiviruses and include African Cassava Mosaic Virus (ACMV), Tomato Golden Mosaic Virus (TGMV), and Maize Streak Virus (MSV). Geminiviruses are subdivided on the basis of whether they infect monocots or dicots and whether their insect vector is a leafhopper or a whitefly. Subgroup I geminiviruses are leafhopper-transmitted that infect monocotyledonous plants (e.g., Wheat Dwarf Virus), Subgroup II geminiviruses are leafhopper-transmitted that infect dicotyledonous plants (e.g., Beet Curly Top Virus), and Subgroup III geminiviruses are whitefly-transmitted that infect dicotyledonous plants (e.g., Tomato Golden Mosaic Virus, TGMV, and African Cassava Mosaic Virus, ACMV). Subgroup I and II geminiviruses have a single (monopartite) genome. Subgroup III geminiviruses have a bipartite genome. For example, TGMV and ACMV consist of two circular single-stranded DNA genomes, A and B, of ca. 2.8 kB each in size. DNA of genome A and DNA of genome B of a given Subgroup III virus have little sequence similarity, except for an almost identical common region of about 200 bp. While both DNA of genome A and DNA of genome B are required for infection, only DNA of genome A is necessary and sufficient for replication and DNA of genome B encodes functions required for movement of the virus through the infected plant.

In both TGMV and ACMV, DNA A contains four open reading frames (ORFs) that are expressed in a bidirectional manner and arranged similarly. The ORFs are named according to their orientation relative to the common region, i.e., complementary (C) versus viral (V) in ACMV and leftward (L) or rightward (R) in TGMV. Thus, ORFs AL1, AL2, AL3, and AR1 of TGMV are homologous to AC1, AC2, AC3, and AV1, respectively, of ACMV. Three major transcripts have been identified in ACMV DNA A and these map to the AV1 and AC1 ORFs, separately and the AC2/AC3 ORFs together. There is experimental evidence for the function of these ORFs. Thus, in ACMV AC1 encodes a replication protein that is essential and sufficient for replication, AC2 is required for transactivation of the coat protein gene, AC3 encodes a protein that is not essential for replication but enhances viral DNA accumulation, and AV1 is the coat protein gene. Except for the essential viral replication protein (encoded by AC1 and AL1 in ACMV and TGMV, respectively), geminivirus replication relies on host replication and transcription machinery. Although geminiviruses are single-stranded plant DNA viruses, they replicate via double-stranded DNA intermediate by 'rolling circle replication'.

Viruses as Expression Vectors

Construction of plant viruses to introduce and express non-viral foreign genes in plants has been demonstrated (U.S. Pat. No. 4,855,237, WO 9534668). When the virus is a DNA virus, the constructions can be made to the virus itself. Alternatively, the virus can first be cloned into a bacterial plasmid for ease of constructing the desired viral vector with the foreign DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA. Alternatively, the cDNA can be cloned behind a heterologous plant promoter, introduced into a plant cell, and used to transcribe the viral RNA that can replicate autonomously [Sablowski et al. (1995) *Proc. Natl. Acad. Sci. USA* vol 92, pp 6901–6905].

Geminiviruses have many advantages as potential plant expression vectors. These include 1) replication to high copy numbers nonsymptomatically, 2) small, well-characterized genomes, 3) assembly into nucleosomes, and 4) nuclear transcription. The DNA A component of these viruses is capable of autonomous replication in plant cells in the absence of DNA B. Vectors in which the coat protein ORF has been replaced by a heterologous coding sequence have been developed and the heterologous coding sequence expressed from the coat protein promoter [Hayes et al.

(1989) *Nucleic Acids Res.* vol. 17, pp. 2391–403; Hayes et al. (1988) *Nature* (London) vol. 334, pp. 179–82].

Greater than fill length copies of wild type TGMV A and B genomes were transformed into petunia [Rogers et al. (1986) *Cell* (Cambridge, Mass.) vol. 45, pp. 593–600]. Replication was reported in the primary transformants and in some of the selfed progeny consistent with its mendelian inheritance, indicating that the chromosomally-integrated master copy, not the replicon, is inherited. This suggests that gametophytic and/or developing seed tissues lack the ability to support replication. The report did not demonstrate whether the virus replicated in non-germinating seed tissue. Prior art shows that geminiviruses are not seed-transmitted in nature [Goodman, (1981) *J. Gen. Virol.* vol. 54, pp. 9–21]. Thus, there was no evidence that they can replicate in gametophytic tissue or developing seed.

Tomato Golden Mosaic Virus (TGMV) DNA A was modified by replacing its coat protein coding sequence with that of NPT II or GUS reporter genes or with that of 35S:NPT II gene and a greater than full length copy of the modified viruses were transformed into tobacco [Hayes et al. (1989) *Nucleic Acids Res.* vol. 17, pp. 2391–403; Hayes et al. (1988) *Nature* (London) vol. 334, pp. 179–82]. Leaves of transgenic plants showed that the high levels of the reporter enzymes was gene copy number-dependent. However, replication of the vector and reporter gene expression were not reported in seed and the genetic stability of the vector in transgenic plants in subsequent generations was not reported. Use of the African Cassava Mosaic Virus (ACMV) in similar fashion has not been reported and it is not known that ACMV DNA or the replication protein(s) can be stably maintained in progeny plants and whether it can replicate in seed tissues.

In one report, a chimeric gene in which the constitutive plant promoter, 35S, was fused to the TGMV sequence containing ORFs AL1, AL2, and AL3 were transformed into *Nicotiana benthamiana*. Different transgenic lines showed significant non-uniformity in the levels of 35S:AL1–3 gene expression as well as their ability to complement viral replication [Hanley-Bowdoin et al. (1989) *Plant Cell* vol. 1, pp. 1057–67]. In another report, chimeric genes in which the constitutive plant promoter, 35S, was fused to the coding sequence of TGMV replication protein AL1 were transformed into tobacco. The expression of TGMV replication protein in the primary transformants supported the replication of a mutant genome A lacking the replication protein. [Hanley-Bowdoin et al. (1990) *Proc. Natl. Acad. Sci. U.S.A.* vol. 87, pp. 1446–50]. However, in both reports neither the genetic stability of the chimeric replication protein gene through subsequent generations nor its ability to support viral replication in seed tissue was reported. In another report, chimeric genes in which the constitutive plant promoter, 35S, was fused separately to the coding sequences of TGMV replication proteins AL1, AL2, and AL3 were transformed into tobacco [Hayes et al. (1989) *Nucleic Acids Res.* vol. 17, pp. 10213–22]. The TGMV replication protein was shown to have been expressed in progeny but the genetic stability of the chimeric replication protein gene through subsequent generations was not reported. Furthermore, it was not reported whether the transgenic plants will support replication in seed tissue.

In another disclosure, Rogers et al. (EP 221044) demonstrated the expression of foreign proteins in plant tissue using a modified "A" genome of the TGMV gemini virus. The foreign gene was inserted in place of the gene encoding the viral coat protein and the resulting plasmid transformed into plant tissue. Rogers et al. did not report tissue specific expression of the foreign protein and are silent as to the genetic stability of the transforming plasmid.

All of the reported viral vectors have a major disadvantage. They were either not shown to be stably maintained in transgenic plants and/or not practically useful. Thus, despite intense efforts to develop plant viral vectors and viruses, no commercially useful plant virus-based recombinant vectors have been developed that are heritable and capable of episomal replication and expression in desired tissue(s) of the transgenic host plant without the need for infection every generation. In fact, replication of plant viruses is expected to be detrimental to the growth and development of plant cells. For example, when greater than full length copy of TGMV genome A is introduced into plant cell one-tenth as many transgenic plants are obtained than when genome B is used or when control transformations are done [Rogers et al. (1986) *Cell* (Cambridge, Mass.) vol. 45, pp. 593–600]. The authors suggest that this may be due to expression of a gene in TGMV A DNA. Furthermore, crude extract of plants expressing tandem copies of both TGMV A and TGMV B genomes are unable to infect *Nicotiana benthamiana* plants. This is consistent with having a low virus titer. Thus, transgenic plants that do regenerate could be selected for low level expression of a toxic viral gene product and low level of viral replication. This is also consistent with the authors' finding that relatively few cells initiate release of the virus, a conclusion based on their observation that most of the tissues remain viable and nonsymptomatic. Similarly, poor replication in transgenic plants containing 35S:replication protein in other reports suggest that plants are either selected for poor expression of the replication protein, presumably because of its toxicity, or that the tissue-specific expression profiles of the replication gene is different from that of viral replication.

Recently, it was reported that 6 of 11 transgenic tobacco plants stably transformed with a monopartite geminivirus (Tobacco Yellow Dwarf Virus) with a functional replication gene showed episomal replication [Needham et al. (1998) *Plant Cell Rep.* vol. 17, pp. 631–639].

Silencing endogenous genes and transgene is an important technology [see Senior et al. (1998) *Biotechnol. Genet. Eng. Rev.* vol. 15, pp. 79–119; Thomas et al. (1998) *Plant Growth Regul.* vol. 25, p. 205]. Silencing of endogenous genes or transgenes by viral infection or by stably incorporated virus in transgenic plants has been reported for RNA virus [Baulcombe et al. PCT Int. Appl. (1998), Ruiz et al. (1998) *Plant Cell* vol. 10, pp. 937–946], Geminiviruses [Kjemtrup et al. (1998) *Plant J.* vol. 14, pp. 91–100, Atkinson et al. *Plant J.* vol. 15, pp. 593–604], and Cauliflower Mosaic Virus [Al-Kaff et al. *Science* (Washington, D.C.) 279:2113–2115 (1998)]. However, regulated virus induced silening in transgenic plants, which is expected to provide regulated gene silencing, has not been reported.

To date, no plant virus-based recombinant vectors are known that are heritable and capable of episomal replication and expression of foreign proteins in target tissue(s) of a transgenic host plant without the need for infection in every generation.

SUMMARY OF THE INVENTION

In one embodiment, the present invention provides a binary transgenic viral expression system for replicating and increasing expression of a target gene comprising
  a) a heritable proreplicon lacking a functional replication gene for autonomous episomal replication and comprising:
    i) cis-acting viral elements required for viral replication;

ii) a target gene comprising at least one suitable regulatory sequence; and iii) flanking sequences that enable the excision of the elements of (i) and (ii); and, b) a heritable chimeric trans-acting replication gene comprising a regulated plant promoter operably-linked to a viral replication protein coding sequence.

In another embodiment, the present invention provides the binary transgenic viral expression system described above but without a target gene, wherein expression of the trans-acting replication gene in cells containing the proreplicon results in replicon replication without a target gene.

The expression system of the present invention is useful for the controlled replication of viral vectors in transgenic plants. Both components of the system are chromosomally-integrated. One component is a chimeric trans-acting replication gene in which the coding sequence of the geminivirus replication protein(s) is placed under the control of a tissue- or development-specific and/or inducible promoter. The second component is a proreplicon, which is unable to replicate by itself but does so in the presence of viral replication protein(s). The two components may be introduced together into a transgenic plant or brought together by crossing transgenic plants carrying the separate components. Also provided are methods of making the expression cassettes and methods of using them to produce transformed plant cells having an altered genotype and/or phenotype.

The principal aspect invention is illustrated in FIG. 1. FIG. 1 illustrates a scheme for transactivating replication of the proreplicon in trans. Regulated expression of a chromosomally integrated chimeric replication gene will result in the release and replication of the replicon from a chromosomally integrated master copy of the proreplicon.

The different components of the invention are heritable independently and may be introduced together into a transgenic plant or brought together by crossing transgenic plants carrying the separate components, such as by the method to produce TopCross® high oil corn seed [U.S. Pat. No. 5,704,160]. Also provided are methods of making the expression cassettes and methods of using them to produce transformed plant cells having an altered genotype and/or phenotype.

BRIEF DESCRIPTION OF FIGURES AND SEQUENCE DESCRIPTIONS

FIG. 1 illustrates excising and activating a proreplicon via the expression of a chimeric trans-acting replication gene.

The invention can be more fully understood from the following detailed description and the accompanying sequence listing. The sequence listings attached hereto comply with the rules governing nucleotide and/or amino acid sequence disclosures in patent applications as set forth in 37 C.F.R. §1.821–1.825.

SEQ ID NOs: 1–14 refer to primers used in the Examples.

DETAILED DESCRIPTION OF THE INVENTION

Figure 1:
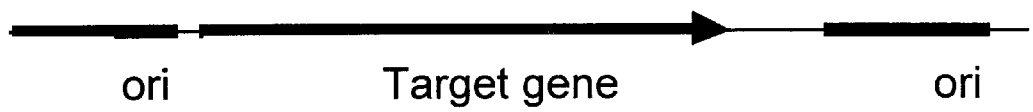
Figure 1:
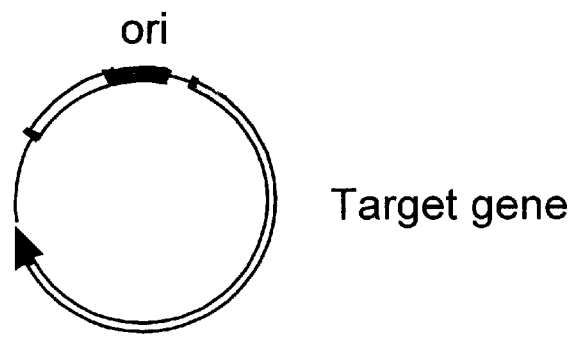

The present invention provides a regulated binary expression system that uses various genetic elements of a plant virus. The expression system is useful for the regulated replicon replication and expression of target genes in plants either for producing foreign proteins or for silencing endogenous plant genes and particularly for achieving stable expression in terminally-differentiated cells.

Applicant has solved the stated problem by providing a two-component, chromosomally-integrated viral expression system comprising a proreplicon and a trans-acting replication gene. The proreplicon contains the cis-acting viral sequences required for replication and a target gene under the control of suitable regulatory sequences. The proreplicon is incapable of self replication in plant cells because it lacks an essential trans-activating replication gene. The second component of the system, a chimeric trans-acting replication gene, consists of a regulated promoter operably-linked to the coding region for a viral replication protein. Expression of the viral replication protein results in the release and replication of the replicon from the proreplicon.

Plant cells containing proreplicon replicate the replicon only in the presence of the replication protein. Thus, regulated expression of the chimeric replication gene in such cells results in regulated replicon replication and target gene amplification. Using the present system, Applicant has demonstrated that (i) soybean and corn seed tissue will support geminivirus replication; and (ii) that the expression system will effect the expression of target genes in transgenic plants. The present invention advances the art by providing plant viral vectors (a) which are maintained stably in the chromosome of transgenic plants; (b) whose replication is controlled by the regulated expression of the replication proteins; and (c) contain nucleic acid sequences that are either homologous to plant endogenous genes or transgenes or that encode foreign proteins that may be produced in the transgenic plant.

The following definitions are to be used to understand the meaning of terms used in this disclosure.

The term "gene" refers to a nucleic acid fragment that expresses mRNA, functional RNA, or specific protein, including regulatory sequences. The term "native gene" refers to a gene as found in nature. The term "chimeric gene" refers to any gene that contains 1) regulatory and coding sequences that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism.

The term "wild-type" refers to the normal gene, virus, or organism found in nature without any known mutation.

The term "genome" refers to the complete genetic material of an organism.

The term "coding sequence" refers to a DNA or RNA sequence that codes for a specific amino acid sequence and excludes the non-coding sequences. The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated. It may be derived from any part of a gene, including its open reading frame, 5' non-coding sequence, or 3' non-coding sequence.

The terms "regulatory sequences" or "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency. (Turner et al. (1995) *Molecular Biotechnology* vol. 3, p. 225).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell vol.* 1, pp. 671–680.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

"Constitutive expression" refers to expression using a constitutive promoter. "Conditional" or "regulated expression" refer to expression using a regulated promoter, respectively. "Constitutive promoter" refers to promoters that direct gene expression in all tissues and at all times. Examples of constitutive promoters include CaMV 35S promoter and nopaline synthase promoter.

"Regulated promoter" refers to promoters that direct gene expression not constitutively but in a temporally and/or spatially regulated manner and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered; numerous examples may be found in the compilation by Okamuro et al. (1989) *Biochemistry of Plants* vol. 15, pp. 1–82. Since in most cases the exact boundaries of regulatory sequences have not been completely defined, DNA fragments of different lengths may have identical promoter activity.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated (such as in early or late embryogenesis), during fruit ripening in developing seeds or fruit, in fully differentiated leaf, or at the onset of senescence.

"Inducible promoter" refers to those regulated promoters that can be turned on in one or more cell types by an external stimulus (such as a chemical, light, hormone, stress, or pathogen).

The term "operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences can be operably-linked to regulatory sequences in sense or anti-sense orientation.

The term "expression" refers to the transcription and stable accumulation of sense (mRNA) or functional RNA. Expression may also refer to the production of protein.

"Altered levels" refers to the level of expression in transgenic organisms that differs from that of normal or untransformed organisms.

"Overexpression" refers to the level of expression in transgenic organisms that exceeds levels of expression in normal or untransformed organisms.

"Antisense inhibition" refers to the production of antisense RNA transcripts capable of suppressing the expression of protein from an endogenous gene or transgene.

The terms "co-suppression" and "transwitch" refer to the production of sense RNA transcripts capable of suppressing the expression of identical or substantially similar transgene or endogenous genes (U.S. Pat. No. 5,231,020).

The term "gene silencing" refers to inhibition or down-regulation of an of an endogenous gene or a transgene that is substanitally similar to the target gene.

The term "homologous to" refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art [as described in Hames and Higgins (eds.) Nucleic Acid Hybridisation, IRL Press, Oxford, U.K.]; or by the comparison of sequence similarity between two nucleic acids or proteins. Homologous genes will be "substantially similar" to each other.

"Substantially similar" refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript.

For example, substantially similar sequences may be defined by their ability to hybridize, under stringent conditions (0.1× SSC, 0.1% SDS, 65° C.), with specifically identified sequences. Preferred substantially similar nucleic acid fragments of the instant invention are those nucleic acid fragments whose DNA sequences are at least 80% identical to specifically identified sequences, either over the entire length of the sequence or over a portion of the sequence. More preferred nucleic acid fragments are at least 90% identical to specifically identified sequences, either over the entire length of the sequence or over a portion of the sequence. Most preferred are nucleic acid fragments that are at least 95% identical to specifically identified sequences, either over the entire length of the sequence or over a portion of the sequence.

The term "binary transgenic viral expression system" describes the expression system comprised of the proreplicon and the chimeric trans-acting replication gene, functioning together to effect the expression of a target gene in a plant. Both elements of the system will be chromosomally-integrated and heritable. Stimulation of the regulated promoter driving the trans-acting gene will cause the expression of viral replication proteins, which will in turn excise the replicon from the proreplicon and initiate replicon replication.

"Binary transgenic viral replication system" refers to a replication system comprised of two chomosomally-integrated elements. The first element is a proreplicon which lacks a target gene encoding a foreign protein. The second element is comprised of a regulated promoter operably-linked to a chimeric trans-acting replication gene. The proreplicon and a chimeric trans-acting gene, functioning together, will effect replication of the proreplicon in a plant in a regulated manner. Such a system is useful where replication of the virus is desired in a regulated manner but where no foreign gene expression is sought. For example, the regulated expression of virus may be useful in conferring resistance to a plant to viral infection.

The term "target gene" refers to a gene on the replicon that expresses the desired target sequence which is either a functional RNA or a mRNA encoding a protein. The target gene is not essential for replicon replication. Additionally, target genes may comprise native non-viral genes inserted into a non-native organism, or chimeric genes and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Proteins encoded by target genes are known as "foreign proteins".

The terms "in cis" and "in trans" refer to the presence of DNA elements, such as the viral origin of replication and the replication protein(s) gene, on the same DNA molecule or different DNA molecules, respectively.

The terms "cis-acting sequence" and "cis-acting element" refer to DNA or RNA sequence, whose function require them to be on the same molecule. An example of a cis-acting sequence on the replicon is the viral replication origin.

The terms "trans-acting sequence" and "trans-acting element" refer to DNA or RNA sequence, whose function does not require them to be on the same molecule. Examples of trans-acting sequence is the replication gene (AC1 or AL1 in ACMV or TGMV geminiviruses, respectively), that can function in replication without being on the replicon.

The term "cis-acting viral sequences" refers to viral sequences that are necessary for viral replication (such as the replication origin) and that are in cis orientation.

The terms "episome" and "replicon" refers to a DNA or RNA vector that undergoes episomal replication in plant cells. It contains cis-acting viral sequences, such as the replication origin, necessary for replication. It may or may not contain trans-acting viral sequences necessary for replication, such as the viral replication genes (for example, the AC1 and AL1 genes in ACMV and TGMV geminiviruses, respectively). It may or may not contain a target gene for expression in the host plant.

The term "replication-defective replicon" refers to a replicon that contains cis-acting viral sequences, such as the replication origin, necessary for replication but defective in an essential replication gene. Consequently, a replication-defective replicon can replicate episomally only when provided with the essential replication protein in trans.

The term "episomal replication" and "replicon replication" refer to replication of DNA or RNA viruses or virus-derived replicons that are not chromosomally-integrated. It requires the presence of viral replication protein(s), is independent of chromosomal replication, and results in the production of multiple copies of virus or replicons per host genome copy. The term "autonomous episomal replication" refers to replication of a replicon that contains all cis- and trans-acting sequences, such as the replication gene, required for replication. Episomal replication does not require the presence of a replication gene provided in trans.

The term "replication origin" refers to a cis-acting replication sequence essential for viral or episomal replication.

The term "proreplicon" refers to a replication-defective replicon that is integrated into a bacterial plasmid or host plant chromosome. It is comprised of cis-acting viral sequences required for replication, and flanking sequences that enable the release of the replicon from it. In addition, the proreplicon may contain a target gene. In the case of RNA viruses, the flanking sequences include regulatory sequences that allow generation of RNA transcripts that can replicate in the presence of replication protein. These regulatory sequences can be for constitutive or regulated expression. Proreplicon lacks a gene encoding a replication protein essential for replication. Therefore, it is unable to undergo autonomous episomal replication but can undergo episomal replication in the presence of the replication protein provide in trans. Thus, its replication requires both release from the integration and the presence of the essential replication gene in trans. The release from integration can be triggered in different ways. For example, in the case of a geminivirus, the proreplicon can be present as a partial or complete tandem duplication, such that a full-length replicon sequence is flanked by virus sequences and such that the duplicated viral sequence includes the viral replication origin. Thus, in this case, the proreplicon serves as a master copy from which replicons can be excised by replicational release in the presence of replication protein(s) [Bisaro, David. Recombination in geminiviruses: Mechanisms for maintaining genome size and generating genomic diversity. Homologous Recomb. Gene Silencing Plants (1994), 219–70. Editor(s): Paszkowski, Jerzy. Publisher: Kluwer, Dordrecht, Germany]. In the case of RNA virus (for example, Brome Mosaic Virus) proreplicons, the amplicon sequences flanking the inactive replicon, which include regulatory sequences, allow generation of the replicon as RNA transcripts that can replicate in trans in the presence of replication protein. These regulatory sequences can be for constitutive or regulated expression.

The terms "viral replication protein" and "replicase" refer to the viral protein essential for viral replication. It can be provided in trans to the replicon to support its replication. Examples include, viral replication proteins encoded by AC1 and AL1 genes in ACMV and TGMV geminiviruses, respectively. Some viruses have only one replication protein, others may have more than one. Viral replication proteins may also include replication proteins of single-stranded RNA viruses, such as the RNA-dependent RNA polymerases, when they can support viral replication in trans, for example Brome Mosaic Virus (BMV).

The term "replication gene" refers to a gene encoding a viral replication protein. In addition to the ORF of the replication protein the replication gene may also contain other overlapping or non-overlapping ORF(s) as found in viral sequences in nature. These additional ORFs (while not essential for replication) may enhance replication and/or viral DNA accumulation. Examples of such additional ORFs are AC3 and AL3 in ACMV and TGMV geminiviruses, respectively.

The term "chimeric trans-acting replication gene" refers to a replication gene in which the coding sequence of a replication protein is under the control of a regulated plant promoter other than that in the native viral replication gene.

The term "chromosomally-integrated" refers to the integration of a foreign gene or DNA construct into the host DNA by covalent bonds.

The term "transformation" refers to the transfer of a foreign gene into the genome of a host organism. Examples of methods of plant transformation include Agrobacterium-mediated transformation (De Blaere et al. (1987) *Meth. Enzymol.* vol. 143, p. 277) and particle-accelerated or "gene gun" transformation technology (Klein et al. (1987) *Nature* (London) vol. 327, pp. 70–73; U.S. Pat. No. 4,945,050). The terms "transformed", "transformant", and "transgenic" refer to plants or calli that have been through the transformation process and contain a foreign gene integrated into their chromosome. The term "untransformed" refers to normal plants that have not been through the transformation process.

The term "transiently transformed" refers to cells in which transgenes and foreign DNA have been introduced (by such methods as agrobacterium-mediated transformation or biolistic bombardment), but not selected for stable maintenance. The term "stably transformed" refers to cells that have been selected and regenerated on a selection media following transformation.

The terms "genetically stable" and "heritable" refer to chromosomally-integrated genetic elements that are stably maintained in the plant and stably inherited by progeny through successive generations.

The terms "primary transformant" and "T0 generation" refer to transgenic plants that are of the same genetic generation as the tissue which was initially transformed, (i.e., not having gone through meiosis and fertilization since transformation).

The terms "secondary transformants" and the "T1, T2, T3, etc. generations" refer to transgenic plants derived from primary transformants through one or more meiotic and fertilization cycles. Secondary transformants may be derived by self-fertilization of primary or secondary transformants or crosses of primary or secondary transformants with other transformed or untransformed plants.

The term "derived from" refers to the obtaining of genetic material from a specific, or identified, source.

The invention provides a two-component, viral expression system for the production of transgenic plants. Both components are chromosomally-integrated and, thus, stably maintained by themselves. One component is the proreplicon that is unable to replicate by itself. The second component is a chimeric trans-acting replication gene in which the coding sequence of a viral replication is operably-linked to a regulated promoter. Expression of the viral replication protein-under appropriate stimulus will result in the release of replicon from the proreplicon and its episomal replication in a cell autonomous manner. Thus, replicon replication can be targeted to specific plant cells by controlling the expression of replication protein(s) to those cells. Plants will be most sensitive to cellular toxicity and/or the detrimental effect of viral replication and/or replication protein(s) in early stages of plant growth and differentiation that involve cell division and differentiation. Thus, controlling the expression of the replication protein and replicon replication entirely or largely to non-dividing, terminally-differentiated cells will reduce the detrimental effect of replicon replication on plant growth and development. Examples of such terminally-differentiated cells include, but are not limited to, the storage cells of seed and root tissues and mature leaf cells. Furthermore, the chromosomally-integrated proreplicon serves as a master copy for replicons not only in different generations but also in the same generation if cell divisions occur after the onset of episomal replication. This strategy will also solve the problem of episomal instability through cell divisions, since episomes are unstable in the absence of selection. Furthermore, replicon replication is expected to achieve high level expression of target genes through gene amplification that is heritable and cell autonomous. The target gene expression can involve either the production of foreign proteins or the silencing of endogenous nuclear gene as well as transgenes by antisense inhibition or co-suppression.

In accordance with the subject invention, novel recombinant virus constructs (including transfer vectors and methods for making them and using them) are described. When used to transform a plant cell, the vectors provide a transgenic plant capable of regulated, high level expression though gene amplification. This regulated expression could be in response to a particular stimulus, such as the development stage, wounding of the plant (for example, by insect attack or pathogen), an environmental stress (such as heat or high salinity), or chemicals that induce specific promoters. Plants in which particular tissues and/or plant parts have a new or altered phenotype may be produced by the subject method.

The constructs include vectors, expression cassettes and binary plasmids depending upon the intended use of a particular construct. Two basic DNA constructs are required which may be combined in a variety of ways for transforming a plant cell and obtaining a transgenic plant. For agrobacterium-mediated transformation, the proreplicon and chimeric replication gene may be combined in one binary plasmid or the two may be introduced into a cell on separate binary plasmids by either co-transformation or sequential transformations. Alternatively, the two constructs may be combined by crossing two transgenic lines containing one or the other construct.

The termination region used in the target gene in the replicon as well as in the chimeric replication protein gene will be chosen primarily for convenience, since the termination regions appear to be relatively interchangeable. The termination region which is used may be native with the transcriptional initiation region, may be native with the DNA sequence of interest, or may be derived from another source. The termination region may be naturally occurring, or wholly or partially synthetic. Convenient termination regions are available from the Ti-plasmid of A. tumefaciens, such as the octopine synthase and nopaline synthase termination regions or from the genes for β-phaseolin, the chemically inducible lant gene, pIN (Hershey et al. (1991) *Plant Mol. Biol.* vol. 17(4), pp. 679–90; U.S. Pat. No. 5,364,780).

The Proreplicon Construct

One basic construct is the proreplicon. In the case of geminiviruses, the proreplicon is preferably present as a partial or complete tandem dimer in T-DNA, such that a single replicon is flanked by cis-acting viral sequences necessary for viral replication, including the replication origin (FIG. 1). These dimers can serve as master copy from which replicons can be excised by replicative release (Bisaro, David. Recombination in geminiviruses:Mechanisms for maintaining genome size and generating genomic diversity. Homologous Recomb. Gene Silencing Plants (1994), 219–70. Editor(s): Paszkowski, Jerzy. Publisher: Kluwer, Dordrecht, Germany) in the presence of the replication protein. The preferable source of proreplicon sequences is from ACMV and TGMV in which the essential replication gene (for example, AC1) is rendered non-functional by mutation (i.e., addition, rearrangement, or a partial or complete deletion of nucleotide sequences). The mutation can be in the non-coding sequence, such as the promoter, or it can be in the coding sequence of the replication protein so as to result either in one or more altered amino acids in the replication protein or in a frame shift. Preferably, the entire replication gene is deleted from the proreplicon such that there is no homology between the transactivating replication gene and the replicon in order to reduce virus-induced homology-based silencing of the trans-activating replication gene during replicon replication. In addition, the proreplicon preferentially has most or all of the coat protein gene which was deleted and replaced by a restriction site for cloning target gene. Proreplicons may also contain a target genes in the replicon sequence. The coding sequence in these target genes are operably-linked to regulatory sequences that are of viral and/or plant origin. One or more introns may be also be present in the cassette. Other sequences, including those encoding transit peptides, secretory leader sequences, or introns, may also be present in the proreplicon and replicon as desired. How to obtain and use these sequences are well known to those skilled in the art. The target gene can encode a polypeptide of interest (for example, an enzyme), or a functional RNA, whose sequence results in antisense inhibition or co-suppression. The nucleotide sequences of this invention may be synthetic, naturally derived, or combinations thereof. Depending upon the nature of the nucleotide sequence of interest, it may be desirable to synthesize the sequence with plant-preferred codons.

It is contemplated that modified proreplicons may be made that have only the minimal origin of replication (ori) sequence. This will allow maximal room for cloning target genes as well as remove all or almost all homology between the proreplicon and the replicase gene to reduce gene silencing of the chimeric replication gene by the chromosomal proreplicon or the episomally replicating replicon. The source of the minimal ori sequence of bipartite geminiviruses can be either DNA from the A genome or DNA from the B genome.

Target genes can encode functional RNAs to silence homologous endogenous genes or transgenes or may encode foreign proteins. Foreign proteins will typically encode non-viral proteins and proteins that may be foreign to plant hosts. Such foreign proteins will include, for example, enzymes for primary or secondary metabolism in plants, proteins that confer disease or herbicide resistance, commercially useful non-plant enzymes, and proteins with desired properties useful in animal feed or human food. Additionally foreign proteins encoded by the target genes will include seed storage proteins with improved nutritional properties, such as the high sulfur 10 kD corn seed protein or high sulfur zein proteins.

The Chimeric Trans-acting Replication Gene Construct

The other basic construct is a chimeric trans-acting replication gene consisting of a regulated plant promoter operably-linked to the coding sequence of a replication protein. For ACMV and TGMV geminiviruses, the replication proteins are encoded by the AC1 and AL1 ORFs, respectively. Also included are 30 the replication proteins of single-stranded RNA viruses, such as the RNA-dependent RNA polymerase encode by the first ORF of potato virus X (PVX) [Angell et al. (1997) *The EMBO Journal,* vol. 16, pp. 3675–3684].

Regulated expression of the viral replication protein(s) is possible by placing the coding sequence of the replication protein under the control of promoters that are tissue-specific, developmental-specific, or inducible.

Several tissue-specific regulated genes and/or promoters have been reported in plants. These include genes encoding the seed storage proteins (such as napin, cruciferin, .beta.-conglycinin, phaseolin), zein or oil bodies proteins (such as oleosin), or genes involved in fatty acid biosynthesis, including acyl carrier protein, stearoyl-ACP desaturase, and fatty acid desaturases (fad 2-1), and other genes expressed during embryo development, such as Bce4, which is expressed at high levels in Brassica seed coat cells is the EA9 gene [see, for example, EP 255378 and Kridl et al. (1991) *Seed Science Research* vol. 1, pp. 209–219]. Particularly useful for seed-specific expression is the pea vicilin promoter [Czako et al. (1992) *Mol. Gen. Genet.* vol. 235(1), pp. 33–40] that has been shown to be seed-specific by the use of diphtheria toxin. Another useful promoter for expression in mature leaves are those that are switched on at the onset of senescence, such as the SAG promoter from Arabidopsis [Gan et al. (1995) *Science* (Washington, D.C.) vol. 270 (5244), pp. 1986–8].

A class of fruit-specific promoters expressed at or during anthesis through fruit development, at least until the beginning of ripening, is discussed in U.S. Pat. No. 4,943,674, the disclosure of which is hereby incorporated by reference. cDNA clones that are preferentially expressed in cotton fiber have been isolated [John et al. (1992) *Proc. Natl. Acad. Sci. U.S.A.* vol. 89(13), pp. 5769–73]. cDNA clones from tomato displaying differential expression during fruit development have been isolated and characterized [Mansson et al. (1985) *Mol. Gen. Genet.* vol. 200, pp. 356–361; Slater et al. (1985) *Plant Mol. Biol.* vol. 5, pp. 137–147]. The promoter for polygalacturonase gene is active in fruit ripening. The polygalacturonase gene is described in U.S. Pat. No. 4,535, 060 (issued Aug. 13, 1985), U.S. Pat. No. 4,769,061 (issued Sep. 6, 1988), U.S. Pat. No. 4,801,590 (issued Jan. 31, 1989) and U.S. Pat. No. 5,107,065 (issued Apr. 21, 1992), which disclosures are incorporated herein by reference.

Mature plastid mRNA for psbA (one of the components of photosystem II) reaches its highest level late in fruit development, in contrast to plastid mRNAS for other components of photosystem I and II which decline to nondetectable levels in chromoplasts after the onset of ripening [Piechulla et al. (1986) *Plant Mol Biol.* vol. 7, pp. 367–376]. Recently, cDNA clones representing genes apparently involved in tomato pollen [McCormick et al., *Tomato Biotechnology* (1987) Alan R. Liss, Inc., New York) and pistil (Gasser et al. (1989) *Plant Cell* vol. 1, pp. 15–24] interactions have also been isolated and characterized.

Other examples of tissue-specific promoters include those that direct expression in leaf cells following damage to the leaf (for example, from chewing insects); in tubers, (for example, patatin gene promoter); and in fiber cells (an example of a developmentally regulated fiber cell protein is E6 [John et al. (1992) Gene expression in cotton (*Gossypium hirsutum L.*) fiber: cloning of the mRNAs. *Proc. Natl. Acad. Sci. U.S.A.* vol. 89(13), pp. 5769–73]). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al. (1997) *Plant Cell* vol. 9, pp. 1527–1545). Other tissue-specific promoters can be isolated by one skilled in the art (see U.S. Pat. No. 5,589,379). Several inducible promoters ("gene switches") have been reported. Many are described in the review by Gatz (1996) *Current Opinion in Biotechnology* vol. 7, pp. 168–172; Gatz (1997) *Annu. Rev. Plant Physiol. Plant Mol. Biol.* vol. 48, pp. 89–108]. These include tetracycline repressor system, Lac repressor system, copper inducible systems, salicylate inducible systems, such as the PR1a system, glucocorticoid [Aoyama et al. (1997) *N-H Plant Journal* vol. 1, pp. 605–612] and ecdysome inducible systems. Also, included are the benzene sulphonamide (U.S. Pat. No. 5,364,780) and alcohol (WO 97/06269 and WO 97/06268)inducible systems and glutathione S-transferase promoters. Other studies have focused on genes inducibly regulated in response to environmental stress or stimuli such as increased salinity, drought, pathogen, and wounding. For example, genes encoding serine proteinase inhibitors, which are expressed in response to wounding in tomato (Graham et al. (1985) *J. Biol. Chem.* vol. 260, pp. 6555–6560; Graham et al. (1985) *J. Biol. Chem.* vol. 260, pp. 6561–6554) and on mRNAS correlated with ethylene synthesis in ripening fruit and leaves after wounding (Smith et al. (1986) *Planta* vol. 168, pp. 94–100). Accumulation of a metallocarboxypeptidase inhibitor protein has been reported in leaves of wounded potato plants [Graham et al. (1981) *Biochem Biophys Res Comm* vol. 101, pp. 1164–1170]. Other plant genes have been reported to be induced methyl jasmonate, elicitors, heat-shock, anerobic stress, or herbicide safeners.

A variety of techniques are available and known to those skilled in the art for introduction of constructs into a plant cell host. These techniques include transformation with DNA employing *A. tumefaciens* or *A. rhizogenes* as the transforming agent, electroporation, particle acceleration, etc. [See for example EP 295959 and EP 138341.] It is particularly preferred to use the binary type vectors of Ti and Ri plasmids of Agrobacterium spp. Ti-derived vectors transform a wide variety of higher plants, including monocotyledonous and dicotyledonous plants, such as soybean, cotton, rape, tobacco, and rice [Pacciotti et al. (1985) *Bio/Technology* vol. 3, pp. 241; Byrne et al. (1987) *Plant Cell, Tissue and Organ Culture* vol. 8, p. 3; Sukhapinda et al. (1987) *Plant Mol. Biol.* vol. 8, pp. 209–216; Lorz et al. (1985) *Mol. Gen. Genet.* vol. 199, p. 178; Potrykus (1985) *Mol. Gen. Genet.* vol. 199, p. 183; Park et al. (1995) *J. Plant Biol.* vol. 38(4), pp. 365–71; Hiei et al. (1994) *Plant J.* vol. 6, pp. 271–282]. The use of T-DNA for transformation of plant cells has received extensive study and is amply described in EP 120516, Hoekema, In: *The Binary Plant Vector System*, Offset-drukkerij Kanters B. V., Alblasserdam, 1985, Chapter V, Knauf, et al., *Genetic Analysis of Host Range Expression by Agrobacterium*, In: *Molecular Genetics of the Bacteria-Plant Interaction*, Puhler, A. ed., Springer-Verlag, New York, 1983, p. 245, and An et al. (1985) *EMBO J.* vol. 4, pp. 277–284. For introduction into plants, the chimeric genes of the invention can be inserted into binary vectors as described in the examples.

Transgenic plant cells are then placed in an appropriate selective medium for selection of transgenic cells which are then grown to callus. From callus 35 shoots are grown and plantlets generated from the shoot by growing in rooting medium. The various constructs normally will be joined to a marker for selection in plant cells. Conveniently, the marker may be resistance to a biocide, particularly an antibiotic (such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription initiation region is derived.

To confirm the presence of the transgenes in transgenic cells and plants, a Southern blot analysis can be performed using methods known to those skilled in the art. Replicons can be detected and quantitated by Southern blot, since they can be readily distinguished from proreplicon sequences by the use of appropriate restriction enzymes. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

The present viral expression system has been used to demonstrate that (i) soybean and corn seed tissue will support geminivirus replication; and (ii) that the expression system will effect expression of foreign genes in tobacco.

More specifically, Applicant has used a transient assay using biolistic bombardment to show that developing soybean and corn seeds can support replication of ACMV-A-derived vector in which the coat protein gene was deleted. Applicant has tested episomal replication of the mutant ACMV-A DNAs in mature tobacco leaf, developing soybean seed embryo (50–150 mg in weight), developing corn seed, and corn suspension cell cultures. For this, a greater than full length copy of mutant ACMV-A DNA is introduced into the tissues by biolistic bombardment and the transiently transformed tissues analyzed by Southern blot for replication. In one mutant, called CP mutant, a 784 bp deletion is made in the coat protein gene from Bam HI site at position 142 to Pml I site at 35 position 926 (with reference to Ssp I in the stem-loop structure of the ori being position 1). In another mutant, called CP+REP mutant, there is a deletion in the replication gene AC1 that was made by deleting 651 bp Bgl II fragment covering AC1, AC2, and AC3 ORFs in addition to the coat protein deletion stated above.

While the CP mutant can replicate episomally by itself, CP+REP mutant cannot. However, CP+REP mutant can replicate episomally in all of the tissues when it is co-bombarded either with CP mutant or with a chimeric replication gene under the control of constitutively expressed 35S promoter or seed-specific phaseolin promoter. Since all of these tissues except the suspension culture are past the cell division stage, this shows that non-dividing, fully or partially differentiated cells are capable of supporting geminivirus replication.

In another embodiment of the expression system, the viral coat protein gene was replaced with a 1.2 kB non-viral gene. Applicant introduced more than full length CP mutant with a 1.2 kB target gene insertion in place of the coat protein into tobacco leaf discs on a binary vector by agrobacterium-mediated transformation. Southern analysis of regenerated shoots showed replication of the modified ACMV-A genome in unrooted shoots but not in rooted shoots. Thus, the CP mutant can tolerate at least a 1.2 kb non-viral DNA insertion. Taken together with the ability of the CP+REP mutant to replicate in trans, it is reasonable to expect that at least 1.85 kb of non-viral DNA can be inserted. Applicant also obtained genetically stable transgenic tobacco plants containing a chromosomally-integrated more than full length of CP mutant. Retransformation of leaf discs of these plants with a chimeric replicase gene resulted in excision and replication of the replicon. Applicant also introduced into tobacco via agrobacterium-mediated transformation native or chimeric ACMV A sequences expressing the leftward open reading frames containing ORFs AC1, AC2, and AC3 under the control of its native promoter or other promoters that are expressed during plant regeneration. However, Southern analysis of transgenic plants showed that these chimeric genes are lost or deleted. Thus, unlike in the case of TGMV, tobacco plants transformed with wild type ACMV DNA A or with greater than full length copy of the coat protein replacement vector showed that the viral sequences were deleted in leaves of rooted transgenic plants. This observation is consistent with the toxicity of replication protein(s) expression, since viral sequences with partially deleted replication protein can be stably maintained. Furthermore, when chimeric genes for expressing the replication protein (s) are introduced into tobacco plants, they were found to be similarly deleted in leaves of rooted transgenic plants. Thus, ACMV replication protein(s) is detrimental to plant regeneration. Applicant has shown that replicase expression is detrimental to plants during plant transformation/regeneration.

Applicant has shown 1) that a wide range of non-dividing tissues (tobacco mature leaf, corn and soybean embryos and corn suspension culture) are capable of supporting geminivirus replication following introduction of the geminivirus by biolistic bombardment and 2) that unrooted stably-transformed shoots also allow replication of geminivirus. The successful use of plant viral vectors will the rely on tightly regulating replication protein expression (and replicon replication) in non-dividing terminally-differentiated cells.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Restriction enzyme digestions, phosphorylations, ligations and transformations were done as described in Sambrook et al., supra. Restriction enzymes were obtained from New England Biolabs (Boston, Mass.), GIBCO/BRL (Gaithersburg, Md.), or Promega (Madison, Wis.). Thermostable DNA polymerase was obtained from Perkin Elmer (Branchburg, N.J.). Growth media was obtained from GIBCO/BRL (Gaithersburg, Md.).

The *Agrobacterium tumefaciens* strain LBA4404 was obtained from Dr. R. Schilperoot, Leiden [Hoekema et al. (1983) *Nature* vol. 303, pp. 179–180].

Transformation Protocols

Biolistic transformations were done essentially as described in U.S. Pat. No. 4,945,050, hereby incorporated by reference. Gold particles (1 mm in diameter) are coated with DNA using the following technique. Ten ug of plasmid DNAs are added to 50 mL of a suspension of gold particles (60 mg per mL). Calcium chloride (50 uL of a 2.5 M solution) and spermidine free base (20 mL of a 1.0 M solution) are added to the particles. The suspension is vortexed during the addition of these solutions. After 10 min, the tubes are briefly centrifuged (5 sec at 15,000 rpm) and the supernatant removed. The particles are resuspended in 200 mL of absolute ethanol, centrifuged again and the supernatant removed. The ethanol rinse is performed again and the particles resuspended in a final volume of 30 uL of ethanol. An aliquot (5 mL) of the DNA-coated gold particles can be placed in the center of a flying disc (Bio-Rad Labs, 861 Ridgeview Dr, Medina, Ohio). The particles are then accelerated into the corn tissue with a PDS-1000/He (Bio-Rad Labs, Medina, Ohio), using a helium pressure of 1000 psi, a gap distance of 0.5 cm and a flying distance of 1.0 cm.

Where Agrobacterium transformations were done the procedure was accomplished were done essentially as described Park et al. (1955) *J. Plant Biol.* vol. 38(4), pp. 365–71.

Transformation And Expression Protocol

Transgenic plants with different constructs will be selected and regenerated into plants in tissue culture by methods known to one skilled in the art and referred to above. The ability of a chimeric, trans-acting replication gene to replicate the replicon from the proreplicon in plant chromosome in trans will be tested following one of the following methods:

1. crossing plants where one parent contains the chimeric replication gene and the other the proreplicon, 2. co-transformaing tobacco leaf discs with two types of Agrobacteria, one containing a binary vector with a plant-selectable marker (such as phosphinothricin resistance) and proreplicon and another containing a binary vector with a different plant-selectable marker (such as kanamycin resistance) and the chimeric replication gene. Transformed leaf discs will be selected and regenerated in the presence of both selection agents, or 3. transforming tobacco with one kind of agrobacteria containing a binary vector with a plant-selectable marker, obtaining regenerated transgenic plant and re-transforming with another kind of agrobacteria containing a binary vector with a different plant-selectable marker. Thus, the first binary vector could contain either the proreplicon or the chimeric replication gene. The binary vector for retransformation will contain the complementary component.

Replication in transgenic plant tissue will be monitored by Southern analysis of genomic DNA (either undigested or following digestion with restriction enzymes) that will distinguish the replicon from chromosomal chimeric replication protein gene and proreplicon by size. Alternatively, replication can be detected by reporter gene expression. For example, increased expression of the GUS reporter genes on the replicon will be assayed by GUS enzyme assay or staining and increased expression of the 10 kD corn storage protein will be detected by western blot using antibodies specific for the 10 kD protein.

Example 1

Tomato Golden Mosaic Virus (TGMV) Constructs
Partial dimer of TGMV with wild-type replication protein (Plasmid pBE651)

Plasmid pCSTA [Von Arnim et al. (1992) *Virology* vol. 186(1), pp. 286–93] was obtained from John Stanley (John Innes Center, Norwich, United Kingdom). It consists of a single complete TGMV-A DNA cloned at its unique Eco RI site into Eco RI site of a plasmid pUC19 derivative. 1922 bp between its Nco I and Sal I sites containing the 3' ends of replication protein AL1 ORF and the coat protein gene were deleted by restriction digestion, fill-in, and self-ligation to result in plasmid pGV650. Then, the Eco RI insert fragment from plasmid pCSTA (containing the complete TGMV-A genome) was cloned in Eco RI site in pGV650 to yield plasmid pGV651. Thus, plasmid pGV651 consists of an intact TGMV-A genome and a tandem duplication of a 570 bp TGMV-A sequence that includes 206 bp TGMV ori sequence and 370 bp 5' AL1 ORF sequence adjacent to the replication origin (ori), such that an intact TGMV-A genome can be made from pGV651 in plant cells either by replicative release or homologous recombination. Plasmid pGV651 can replicate in a plant cell when introduced by biolistic bombardment. The Hind III fragment of pGV651 carrying the TGMV dimer with wild-type AL1 ORF was cloned into pBin19 [Frisch et al., (1995) *Plant Mol. Biol.* vol. 27(2), pp. 405–409] such that the AC1 gene is transcribed away from the Nos:NPT II gene. The resultant binary plasmid pBE651 was introduced into tobacco plants via *Agrobacterium tumefaciens* strain LBA4404.
Partial dimer of TGMV with wild-type replication protein and GUS reporter (plasmid pBE671)

The unique BstB1 site in plasmid pGV651 was converted to Not I following BstB1 digestion, fill-in reaction, and ligation to Not I linkers (New England Biolabs catalog number 1125) to result in pGV652. Then, a 1401 bp Not I-Sac I fragment (containing the coat protein gene in plasmid pGV652) was replaced with a 2545 bp Not I-Sac I fragment from plasmid pGV662 (see below) containing the GUS [Jefferson et al., The use of the *Escherichia coli* b-glucuronidase gene as a gene fusion marker for studies of gene expression in higher plants. *Biochem. Soc. Trans.* (1987), vol. 15(1), pp. 17–18] to yield plasmid pGV671. In plasmid pGV671, GUS expression is under the control of the coat protein promoter. Plasmid pGV671 can replicate when introduced into plant cells by biolistic bombardment. The Hind III fragment carrying the dimer will be cloned into a binary vector pBin19 to result in pBE671 and transferred to plants as known to one skilled in the art.
TGMV proreplicon without GUS reporter gene (plasmid pGV654)

Plasmid pGV654 was made from plasmid pGV652 (see description above) by deleting a 895 bp region between Bam HI-Eco RI including 709 bp of the 3' end of AL1 ORF and the 5' regions of AL2 and AL3 ORFs following restriction digestion, fill-in, and ligation. When introduced into plant cells by biolistic bombardment the proreplicon in plasmid pGV654 was unable to replicate without the gene encoding the replication protein in trans.
TGMV proreplicons with GUS reporter gene (plasmids pGV662 and pGV672)

Three different TGMV proreplicons with GUS reporter gene will be introduced into plant cells. They differ in the kind of mutation in the replication gene. Two (pGV662 and pGV672) were made by deletions of different sizes and one is being made by introducing a frameshift mutation.

The 696 bp Not I-Nco I fragment in plasmid pGV654 (containing most of the coat protein gene) was replaced with a 1875 bp Not I-Nco I fragment containing the GUS ORF (the Nco I site includes the initiation codon) to yield plasmid pGV661. Since the Nco I site is downstream of the coat protein initiation codon, a modified coat protein promoter with a Nco I in the 5' untranslated region was made by nucleic acid amplification using primers [(See U.S. Pat. Nos. 4,683,195; 4,683,202; 4,965,188 to polymerase chain reaction (PCR), 5'-CGTCCGGATCCAATTCTCCCCATACAA-GAGTATCT-3' [SEQ ID NO: 1] and 5'-GTCGACCCATG-GTTAAAGATCCACGAAACGCATGT [SEQ ID NO:2] on plasmid pCSTA by 40 cycles of 60° C., 1' annealing; 90° C., 2'. A 663 bp Bam HI+Nco I fragment derived from the PCR product and containing the ori, and coat protein promoter without any coat protein coding sequence was used to replace the corresponding 698 bp Bgl II-Nco I fragment of plasmid pGV661 to result in plasmid pGV662.

Another replication gene deletion was made by the deletion of 772 bp between Xmn I site in AL1 ORF and Swa I site in AL3 ORF. For this, plasmid pGV671 was digested with Swa I and partial Xmn I and then religated. Plasmids pGV662 and pGV672 differ from their wild-type counterpart, plasmid pGV671, in having deletions in AL1, AL2 and AL3 ORFs of 709 bp and 433 bp, respectively. The Hind III fragment of plasmid pGV662 was isolated and cloned into the Hind III site of pBin19 and pGV674 to yield binary plasmids pBE662 and pBE675, respectively. The Hind III fragment of pGV672 was cloned into pGV674 to yield pBE672. Binary vector pGV674 was made by replacing the Bsu 36 I-Cla I fragment in pBin19 (carrying the nopaline synthase promoter:npt II:3'nopaline synthase chimeric gene that confers resistance to kanamycin in plants) with a Bsu 36 I-Cla I (fragment carrying the nopaline synthase promoter:bar:3'nopaline synthase chimeric gene that confers resistance to phosphonithricin herbicide). pBE662 binary plasmid was introduced into plants via *Agrobacterium tumefaciens* LBA4404-mediated transformation known to one skilled in the art. [Walden, Vector Systems for Agrobacterium-mediated Transformation In Method Plants Biochem. (1997), 106 (Molecular Biology), 85–102.]

Example 2

Chimeric Trans-acting TGMV Replication Genes
35S:TGMV replication gene (plasmid pGV653)

Plasmid pGV653 was derived from plasmid p35S-GFP plant vector (Promega Corp., 7113 Benhart Dr., Raleigh, N.C.) by replacing the first 462 bp of the upstream region (between Hind III and Acc I) of 35S promoter with Not I and then the Bam HI-Sac I fragment containing the green fluoroscent protein ORF (between the 35S promoter and 3' region of nopaline synthase gene) with that of TGMV sequence containing AL1, AL2, and AL3 ORFs. For the latter, a Bam HI site was introduced at position 29 [Hamilton et al., *EMBO J*. 3:2197–205 (1984)] in the 5' untranslated region (16 bp upstream of the AL1 ORF) of TGMV AL1 gene and the 2976 bp of Bam HI-Bam HI-Sac I TGMV sequence was used to replace the Bam HI-Sac I region to form pGV653.

Chemically-inducible promoter In 2-2:TGMV replication gene (plasmid pBE665)

The Mfe I and BstB1 sites in plasmid pGV651 were converted to Spe I following fill-in and ligation of Spe I linker (New England Biolab, catalog no. 1087). The 1603 bp Spe I fragment (containing the TGMV AL1, AL2, and AL3 ORFs) was isolated and cloned between the inducible promoter 2-2 and the 3' region of 2-1 gene in plasmid pGV664 to yield plasmid pGV665. Plasmid pGV664 was derived from pGV659 (see description below) by replacing its Not I-Spe I fragment (containing 2-2 promoter and ACMV replication protein gene), with that of a 2-2 promoter in which the Nco I site was modified to Spe I site. The latter was made by PCR such that the Nco I site at its 3' end was replaced by the Spe I site, the Spe I site at the 5' end of the promoter was destroyed, and the Bam HI site at the 5' end was changed to Bgl II. The 2561 bp BglII-Asp718 fragment from pGV665 containing the 2-1IN promoter:T-Rep ORF:3' 2-2 chimeric gene was isolated from pGV665 and cloned into binary vector pBin19 cut with BamHI-Asp718 to result in pBE665. The chimeric gene was introduced into tobacco plants via *Agrobacterium tumefaciens* LBA4404.

Several shoots from each transformation of *Nicotiana benthamiana* with both BA662 and BA665 rooted and regenerated into plants. All plants lacked any observable abnormal phenotype. Applicant obtained one plant positive for the presence of the transgene (determined by Southern blot) from each of the BA662 and BA665 transformations. These plants were either selfed or crossed with each other both ways.

Seeds from the reciprocal crosses were planted on soil flats and allowed to germinate in the growth chambers. 48 and 72 progeny seedlings from BA662×BA665 and BA665× BA662 crosses, respectively, were transplanted on a gridded flat. The phenotypes of the plants were relatively normal except that the seedlings varied in sizes and some of the leaves appeared crinkled as also observed on seed germination plates. Four leaf discs were punched out from a leaf in each plant and a pair of discs were placed in one well of two different 96 well plates containing agar with Murashige and Skoog salts, 30 g of sucrose, and no hormones. The wells of one plate were flooded with 1 mL of the 30 mg/L 2-CBSU for 30 min and then the liquid was removed without rinsing. One disc from each well was tested for GUS staining after 24 and 72 hrs. Out of 48 treated BA662× BA665 seedlings, 3 showed GUS staining after 24 hrs and 10 more after 72. Out of 72 of treated BA665×BA662 seedlings, 8 showed GUS staining after 24 hrs and 23 after 72 hrs. Only discs from the strongest GUS-expressing seedlings showed trace GUS activity without safener treatment. This 'leaky' induction may be attributed to wounding and growth on agar. The degree of staining varied not only between different GUS-positive discs but also across a disc. After 72 hours there were not only many more individuals that stained positive compared to 24 hrs but the ones that stained after 24 hrs stained also more heavily after 72 hrs. This indicated that the virus was replicating.

Proreplicon replication was confirmed by Southern analysis confirmed that all GUS-positive plants tested were positive for both IN:Rep and proreplicon. The genomic DNA was isolated from leaves of the six highest GUS-expressing plants (three each from BA662×BA665 and BA665×BA662 progeny) either without or with 2-CBSU treatment. For the former, genomic DNA was isolated from freshly harvested leaves. For the latter, leaves were cut in strips, placed on agar, treated with 30 mg/L 2-CBSU for 30 min, and placed on agar for 3 days after removing the safener. No replicon was detected in untreated leaves and a large increase in replicon copy number was detected in treated leaves.

Seed-specific vicilin promoter:TGMV replication gene

Plasmid pGV656 (containing a 3086 bp Hind III fragment containing a chimeric corn 10 kD storage protein ORF under the control of seed-specific vicilin promoter) was made. The chimeric gene consists of 1) an operably-linked 2308 bp Hind III-Nco I vicilin promoter isolated from plasmid pGA971 [Czako et al. (1992) *Mol. Gen. Genet.* vol. 235(1), pp. 33–40] and 2) the 276 bp Sac I-Hind III fragment containing a 3' untranslated region of nopaline synthase promoter. The 394 bp Spe I-Xba I fragment containing most of the 10 kD ORF was replaced by the 1604 bp Spe I fragment containing AC1–3 ORFs. (This fragment was made by adding Spe I linker to Mfe I and Bst BI digested TGMV clone, described above). The 56 bp between the Nco I and Spe I sites was deleted by PCR. The 4236 bp Hind III fragment (containing the chimeric vicilin promoter:TGMV replication protein ORF:3' nopaline synthase gene) was cloned into the Hind III site of pBin19 binary vector. The resultant binary plasmid pBE679 was introduced into tobacco plants via *Agrobacterium tumefaciens* LBA4404-mediated transformation known to one skilled in the art. The transgenic plants are in pots and will be crossed with transgenic plants containing the proreplicon BA662 (see above).

Senecence-associated promoter SAG:TGMV replication gene (plasmid pBE667)

The 1.6 kB Spe I fragment containing the TGMV AL1, AL2, and AL3 ORFs (described above) was cloned in the Xba I site of plasmid pGV666, downstream of a senescence associated (SAG) promoter. pGV666 was derived from plasmid pSG516 [Gan et al. (1995) *Science* (Washington, D.C.) vol. 270(5244), pp. 1986–8] by replacing its Bst B1-Sac I fragment (containing 3' end of the promoter and isopentenyl transferase ORF) with a BstB I-Sac I fragment (containing SAG promoter modified by PCR) to replace the Nco I site with Xba I/Sac I sites. The 3801 bp Spe I-Sac I fragment (containing the SAG promoter:TGMV replication gene) was isolated from pGV667 and cloned into Xba I-Sac I digested vector pBI101 (Clonetech Inc., 6500 Donlon Rd, Somis, Calif.) to yield binary plasmid pBE667 such that the SAG promoter:ACMV replication gene is operably-linked to the 3' untranslated region of nopaline synthase gene. The chimeric gene in pBE667 was introduced into plants via *Agrobacterium tumefaciens* LBA4404-mediated transformation known to one skilled in the art.

Example 3

African Cassava Mosaic Virus (ACMV) Constructs
Partial dimer of ACMV with wild-type replication gene (plasmid pGV596)

Plasmid pCLVO12 (ATCC 45039), which contains DNA A of African Cassava Mosaic Virus [West Kenyan isolate 844, Stanley et al. (1983) *Nature* vol. 301, pp. 260–262] was linearized with Pml I and ligated to Bam HI linker (New England Biolab cat. no. 1071). Following Bam HI digestion, the 2 kB fragment containing the ori and AC1–3 ORFs was isolated and cloned into Bam HI site of pSK to yield pGV592 and pGV592R. These plasmids differ in insert orientation: the coat protein promoter is proximal to the Sal site in the vector in pGV592 and distal in pGV592R. BstB1 site in AC1 gene in pGV592R was modified to Sac II, following restriction digestion, fill-in, and Sac II linker ligation. The 358 bp Not I-Sac II fragment was isolated and cloned between the Not I-Sac II cleaved pGV592 to yield pGV596a. Deletion of 140 bp between Sna B 1 and Not I sites in pGV596a containing the 3' end of the residual ACMV coat protein gene following Sna BI digestion, Not I linker (New England Biolabs, catalog no. 1125) ligation, Not I digestion, and self ligation yielded pGV605. Both plasmids pGV596a and pGV605 can replicate when introduced singly into plant cells by biolistic bombardment.

ACMV proreplicon (plasmid pGV596D)

Deletion of a 651 bp region between the Bgl II sites that includes the 3' end of AC1 gene in pGV596a yielded ACMV proreplicon (plasmid pGV596D).

ACMV proreplicons with reporter gene (plasmids pGV614D and pGV616D)

Plasmid pGV605 was modified by converting its Sac I site to Asp718 and by destroying the Bam HI site near Sal I to form plasmid pGV611. Chimeric 10 kD corn storage protein gene under the control of either a seed-specific or constitutively-expressed promoter was used as a reporter for gene expression. The seed-specific chimeric gene was cloned as a 1164 bp Bam HI-Bgl II fragment in the Bam HI site of pGV611 to yield plasmid pGV614. It consists of an operably-linked 383 bp of seed-specific phaseolin promoter (from −295 to +82 bp with respect to the transcription start site), 450 bp containing the 10 kD ORF, and 331 bp containing 279 bp of the 3' untranslated region of nopaline synthase promoter. For the constitutive reporter gene, plasmid pGV611 was first modified to delete the sites between Not I and Bam HI by Bam HI digestion, fill-in, addition of Not I linker (New England Biolabs, catalog no. 1125), and religation to yield plasmid pGV611N. Then, the constitutive chimeric gene was cloned as a 1194 bp Not I fragment in the Not I site of pGV611N to yield plasmid pGV616. It consists of an operably-linked 411 bp constitutively expressed 35S promoter (from −400 to +11 bp with respect to the transcription start site), 460 bp containing the 10 kD ORF, and 323 bp containing 279 bp of 3' untranslated region of nopaline synthase promoter. Deletion of a 651 bp region between the Bgl II sites that includes the 3' end of replication gene AC1 in pGV614 and pGV616 yielded ACMV proreplicons with the reporter gene, pGV614D and pGV616D, respectively. Plasmids pGV614D and pGV616D were linearized with Sal I enzyme and cloned into the Sal I site of binary plasmid pZBL1 and introduced into tobacco plants via *Agrobacterium tumefaciens* LBA4404.

Chimeric ACMV Replication genes; Seed-specific phaseolin promoter:ACMV replication gene Plasmid pCLVO12 (ATCC 45039) containing ACMV DNA was modified by creating an Nco I site at the initiation codon of AC1 ORF by PCR and by modifying Pml I site at the 3' end of the coat protein gene to Xba I site. The 1685 bp Nco I-Nco I-Xba I fragment containing AC1–3 ORFs was used to make seed-specific chimeric replication genes. The chimeric phaseolin:replication gene consists of an operably-linked 384 bp Bam HI-Nco I fragment containing 374 bp of seed-specific phaseolin promoter (from −292 to +82 bp with respect to the transcription start site), 1685 bp containing AC1–3 ORFs (see above), and 323 bp containing 279 bp of the 3' untranslated region of nopaline synthase promoter. The phaseolin:ACMV AC1 ORF fusion (without the 3' nopaline synthase promoter) will be isolated as a 2120 bp Bam HI-Sac I fragment and cloned into the Bam HI-Sac I sites of binary vector pBI101 (Clonetech Co., 6500 Donlon Rd, Somis, Calif.) to yield binary plasmid pBE625 such that the phaseolin promoter:ACMV AC1 ORF is operably-linked to the 3' untranslated region of nopaline synthase gene. The chimeric gene in pBE625 will be introduced into plants via *Agrobacterium tumefaciens* LBA4404-mediated transformation known to one skilled in the art.

Seed-specific vicilin promoter:ACMV replication gene

Plasmid pGV656 containing a 3086 bp Hind III fragment containing a chimeric corn 10 kD storage protein ORF under the control of seed-specific vicilin promoter was made. The chimeric gene consists of 1) an operably-linked 2308 bp Hind III-Nco I vicilin promoter isolated from plasmid pGA971 [Czako et al. (1992) *Mol. Gen. Genet.* vol. 235(1), pp. 33–40] and 2) a 276 bp Sac I-Hind III fragment containing the 3' untranslated region of nopaline synthase promoter. The 450 bp Nco I-Xba I fragment containing 10 kD ORF will be replaced by the 1685 bp Nco I-Nco I-Xba I fragment containing AC1–3 ORFs (see description above). The 4321 bp Hind III fragment containing the chimeric vicilin promoter:ACMV replication protein ORF:3' nopaline synthase gene will be cloned into the Hind III site of pBin19 binary vector and introduced into tobacco plants via *Agrobacterium tumefaciens* LBA4404-mediated transformation known to one skilled in the art.

Chemically-inducible promoter In 2-2:ACMV replication gene (plasmid pBE659)

Plasmid pCLVO12 (ATCC 45039) containing ACMV DNA was modified by creating an Nco I site at the initiation codon of AC1 ORF by PCR and by converting Sna B1 site at the 3' end of the coat protein gene [Stanley et al. (1983) *Nature* vol. 301, pp. 260–262 (1983)] to multiple cloning sites (Not I, Xba I, Spe I, and Bam HI sites). The Nco I-Nco I-Bam HI fragment (containing the ACMV ORFs AC1, AC2, and AC3) was isolated and cloned between the Nco I and Bgl II sites in H. Hershey's pIN2-1-2 vector (supra) yielding plasmid pGV659. Plasmid PGV659 consists of a 452 bp Bam HI-Nco I fragment (sequence shown in FIG. 4 of U.S. Pat. No. 5,364,780) containing corn gene 2-2 promoter [Hershey et al., Isolation and characterization of cDNA clones for RNA species induced by substituted benzenesulfonamides in corn. *Plant Mol. Biol.* (1991), 17(4), 679–90)], followed by 960 bp of Nco I-Nco I-Bam HI fragment (see above), and a 496 bp Bgl II-Asp718 I fragment containing the 3' non-coding region from corn gene 2-1 [Hershey et al., Isolation and characterization of cDNA clones for RNA species induced by substituted benzene-sulfonamides in corn. *Plant Mol. Biol.* (1991), 17(4), 679–90; U.S. Pat. No. 5,364,780]. The 2538 bp Bam HI-Asp 718I fragment in pGV659 containing operably-linked chemically-inducible in 2-2 promoter, AC1–3 ORFs, and 247 bp of the 3' untranslated region of corn gene 2-1 will be isolated and cloned into Bam HI-Asp718 sites of pBin19 binary vector and the resultant binary vector will be introduced into plants via *Agrobacterium tumefaciens* LBA4404-mediated transformation known to one skilled in the art.

Senecence-associated promoter SAG:ACMV Rep (plasmid pBE640)

A 1737 bp Nco I-Nco I-Sac I fragment containing ACMV AC1–3 ORFs was cloned into Nco I-Sac I-digested plasmid pSG516 [Gan et al. (1995) *Science* (Washington, D.C.), vol.270(5244), pp. 1986–8] to yield plasmid pGV640. A 3924 bp Spe I-Sac I fragment from pGV640 (containing the SAG promoter operably-linked to the ACMV Rep ORF) will be isolated and cloned into Xba I-Sac I digested pB 1101 to yield binary plasmid pBE676 such that the SAG promoter-:ACMV Rep is operably-linked to the 3' untranslated region of nopaline synthase gene. The chimeric gene in pBE676 will be introduced into plants via via *Agrobacterium tumefaciens* LBA4404-mediated transformation known to one skilled in the art.

Example 4

Construction of Modified Proreplicons

Modified proreplicons with minimal ori will be made as follows:

The 101 bp minimal TGMV-A ori sequence [positions 53 to 153, Orozco et al. (1998) *Virology* vol. 242, pp. 346–356] will be isolated as a PCR product using PCR primers P1 and P2 on pGV662 template DNA. Primer P1 will have a Not I restriction site adjacent to position 53 of the ori and primer P2 will have a Sal I site adjacent to ori position 153. Following Not I-Sal I digestion, the PCR product will be cloned into Not I-Sal I digested pGV662. The resultant plasmid, pGV662A, will have the ori and the mutant AL1 in pGV662 replaced with the 101 bp minimal ori.

A 192 bp sequence containing the polyadenylation sequence of CaMV [positions 7440–7638, Gen bank accession #s V00140 J02046] will be isolated as a PCR product B using PCR primers P3 and P4. Primer P3 will have a Xba I restriction site adjacent to position 7440 and primer P4 will have a Bam HI I site adjacent to position 7638. A 262 bp sequence containing the polyadenylation sequence of nopaline synthase gene (positions 2068–2344, Gen Bank ACCESSION J01541 V00087) will be isolated as a PCR product C using PCR primers P5 and P6. Primer P5 will have a Not I restriction site adjacent to position 1068 and primer P6 will have a Bgl II site adjacent to position 2344. Bam HI-digested PCR product B and Bgl 11-digested PCR product C will be ligated and the Bam HI- and Bgl II-resistant ligation product will be subjected to PCR using primers P3 and P6. The resultant 454 bp PCR product comprised of inverted (head-to-head) polyadenylation sequences will be digested with Xba I and Not I and cloned between the Xba I and Not I sites in the 3' untranslated region following the GUS ORF in plasmid pGV662A, such that in the resultant plasmid, pGV662B, the GUS transcript will be polyadenylated using the CaMV polyadenylation signal sequence and the transcript from the ALI promoter in the ori will be polyadenylated using the nos polyadenylation signal sequence.

A 275 bp of TGMV A sequence [positions 53–228, Orozco et al. (1998) *Virology* vol. 242, pp. 346–356] containing the minimal TGMV-A ori sequence and the coat protein promoter will be isolated as PCR fragment E using PCR primers P7 and P8 on plasmid pGV662 template DNA. Primer P7 will have a Sac I restriction site adjacent to position 53 and Primer P8 will have a Xho I-Nco I sites adjacent to position 228. Following digestion with Sac I and Nco I the 275 bp sequence containing the minimal ori and coat protein promoter will be cloned in Sac I-Nco I digested pGV662B to resulat in plasmid pGV662C.

The 101 bp minimal TGMV-A ori sequence [positions 53 to 153, Orozco et al. (1998) *Virology* vol. 242, pp. 346–356 (1998)] will also be isolated as a PCR product F using PCR primers P9 and P10 on pGV662 template DNA. Primer P9 will have a Sac I restriction site adjacent to position 53 of the ori and Primer P10 will have a Bgl II site adjacent to ori position 153. The phaseolin promoter will be isolated as a 323 bp PCR product G using primers P11 and P12 on a previously described plasmid pGV614 template DNA. Primer P11 has a Bam HI restriction site adjacent to position −295 (Bcl I site) and Primer P12 has a Nco I site at to position +20 (Sca I site) with respect to the transcription start site of phaseolin promoter [Bustos et. al. (1991) *EMBO J.* vol. 10, pp. 1469]. Bgl II-digested PCR product F and Bam HI-digested PCR product G will be ligated and the Bam HI- and Bgl II-resistant ligation product will be subject to PCR using primers P9 and P12. The resultant 424 bp PCR fragment, containing the minimal ori and phaseolin promoter, will be cloned in pGV662 following Sac I-Nco I digestion to result in pGV662D.

pGV662C and pGV662D will be modified pGV662, in which the GUS target gene will be under the control of the coat protein promoter or phaseolin promoter, respectively. The GUS sequence will be replaced by other target genes. These modified plasmids will be cloned as a Hind III fragment into a binary plasmid and used to transform transgenic plants as described above.

The sequences of PCR primers (with the introduced site underlined) used above are given below:

| | | |
|---|---|---|
| P1: | 5'-GCT<u>GCGGCCGC</u>TCCAAAAGTTATATGAATTGGTAAGGT-3' | [SEQ ID NO:3] |
| P2: | 5'-CGA<u>GTCGAC</u>GCGCGGCCATCCGGTAAT-3' | [SEQ ID NO:4] |
| P3: | 5'-GCAGGATCCACTGGATTTTGGTTTTAGGA-3' | [SEQ ID NO:5] |
| P4: | 5'-GCATCTAGAAAATCACCAGTCTCTCTCTACA-3' | [SEQ ID NO:6] |
| P5: | 5'-GCTGCGGCCGCTGGAGTAAAGAAGGAGTG-3' | [SEQ ID NO:7] |
| P6: | 5'-GCCAGATCTAGTAACATAGATGACACCG-3' | [SEQ ID NO:8] |
| P7: | 5'-CGT<u>GAGCTC</u>TCCAAAAGTTATATGAATTGGTAGTAAGGT-3' | [SEQ ID NO:9] |

-continued

P8:  5'-C<u>CTCGAGCATGG</u>TTTGAATTAAAGATCCACGAAA-3'    [SEQ ID NO:10]

P9:  5'-CGT<u>GAGCTC</u>TCCAAAAGTTATATGAATTGGTAGTAAGGTAAGGT-3'    [SEQ ID NO:11]

P10: 5'-GGT<u>AGATCT</u>GCGCGGCCATCCGGTAAT-3'    [SEQ ID NO:12]

P11: 5'-CAC<u>GGATCC</u>AGATCGCCGCGTC-3'    [SEQ ID NO:13]

P12: 5'-C<u>CTCGAGCCATGG</u>ACTCTGGATGGATGGATGATG-3'    [SEQ ID NO:14]

---

What is claimed is:

1. A binary transgenic viral expression system for replicating and increasing expression of a target gene comprising:
   a) a heritable, chromosomally-integrated proreplicon lacking a functional replication gene for autonomous episomal replication, and comprising:
      i) cis-acting viral elements required for viral replication;
      ii) a target gene comprising at least one suitable regulatory sequence; and
      iii) flanking sequences that enable the excision of the elements of i) and ii); and
   b) a heritable, chromosomally-integrated chimeric trans-acting replication gene comprising a regulated plant promoter operably-linked to a viral replication protein coding sequence, wherein said cis-acting viral elements and said viral replication protein coding sequence are derived from the same virus.

2. The binary transgenic viral expression system of claim 1 wherein the proreplicon and the trans-acting replication gene are derived from any geminivirus.

3. The binary transgenic viral expression system of claim 2 wherein the geminivirus is selected from the group consisting of TGMV and ACMV.

4. The binary transgenic viral expression system of claim 1 wherein the regulated plant promoter is selected from the group consisting of tissue-specific promoters, inducible promoters, and development stage promoters.

5. The binary transgenic viral expression system of claim 4 wherein the regulated plant promoter is selected from the group consisting of promoters derived from genes from safener-inducible systems, tetracycline-inducible systems, salicylate-inducible systems, alcohol-inducible systems, glucocorticoid-inducible systems, and ecdysome-inducible systems.

6. The binary transgenic viral expression system of claim 1 wherein the heritable, chromosomally-integrated chimeric trans-acting replication gene comprises at least one open reading frame selected from the group consisting of AC1, AL1, AC2, AL2, AC3, and AL3.

7. The binary transgenic viral expression system of claim 1 wherein the target gene encodes a protein selected from the group consisting of an enzyme, a structural protein, a seed storage protein, a protein that conveys herbicide resistance, and a protein that conveys insect resistance.

8. The binary transgenic viral expression system of claim 1 wherein the target gene encodes a functional RNA whose expression produces an altered plant trait.

9. The binary transgenic viral expression system of claim 1 wherein the at least one suitable regulatory sequence of the target gene is selected from the group consisting of constitutive promoters, plant tissue-specific promoters, development-specific promoters, inducible promoters and viral promoters.

10. The binary transgenic viral expression system of claim 9 wherein the at least one suitable regulatory sequence is selected from the group consisting of a viral coat protein promoter, the nopaline synthase promoter, the phaseolin promoter, and the cauliflower mosaic virus promoter.

11. The binary transgenic viral expression system of claim 1 wherein the proreplicon optionally contains a DNA fragment encoding a transit peptide.

12. A method of altering the expression of an endogenous plant gene or transgene in a plant comprising:
   a) transforming a plant with the binary transgenic viral expression system of claim 1, wherein the target gene encodes at least one functional RNA having substantial similarity to an endogenous plant gene or transgene of the plant; and
   b) growing the transformed plant of a) under conditions wherein the at least one functional RNA is expressed, the expression of the at least one functional RNA inhibiting the substantially similar endogenous plant gene or transgene in a plant.

13. A method of altering the levels of a protein encoded by a target gene in a plant comprising:
   a) transforming a plant with the binary transgenic heritable viral expression system of claim 1; and
   b) growing the transformed plant under conditions wherein the protein is expressed.

14. The method of claim 13 wherein the target gene is in sense orientation and the level of the expressed protein is increased.

15. A method of altering the levels of a protein encoded by a target gene in a plant comprising:
   a) transforming a first plant with a proreplicon to form a first primary transformant, the proreplicon lacking a functional replication gene for autonomous episomal replication and comprising:
      (i) cis-acting viral elements required for viral replication;
      (ii) a target gene comprising at least one suitable regulatory sequence; and
      (iii) flanking sequences that enable the excision of the elements of (i) and (ii); and
   b) transforming a second plant with a chimeric trans-acting replication gene to form a second primary transformant comprising a regulated promoter operably-linked to a viral replication protein coding sequence, wherein said cis-acting viral elements and said viral replication protein coding sequence are derived from the same virus;
   c) growing the first and second primary transformants wherein progeny from both plants are obtained; and
   d) crossing the progeny of the first and second primary transformants to yield plants in which the target gene is expressed.

16. A binary transgenic viral replication system for replicon replication comprising in a cell:
   (a) a chromosomally-integrated heritable proreplicon lacking a functional replication gene for autonomous episomal replication and comprising cis-acting viral elements required for viral replication and flanking sequences for the excision of the proreplicon from the chromosome, and
   (b) a heritable chimeric trans-acting replication gene comprising a regulated plant promoter operably-linked to a viral replication protein coding sequence, wherein said cis-acting viral elements and said viral replication protein coding sequence are derived from the same virus.

17. The transgenic viral replication system of claim 16 wherein the proreplicon and the trans-acting replication gene are derived from any geminivirus.

18. The transgenic viral expression system of claim 17 wherein the geminvirus is selected from the group consisting of TGMV and ACMV.

19. The viral replication system of claim 16 wherein the regulated plant promoter is selected from the group consisting of tissue-specific promoters, inducible promoters and development stage-specific promoters.

20. The viral replication system of claim 19 wherein the regulated plant promoter is selected from the group of promoters derived from genes from safener-inducible systems, from tetracycline-inducible systems, from salicylate-inducible systems, from alcohol-inducible systems, from glucocorticoid-inducible systems, and from ecdysome-inducible systems.

21. The viral replication system of claim 16 wherein the heritable chimeric trans-acting replication gene comprises at least one open reading frame selected from the group consisting of AC1–3 of ACMV and AL1–3 of TGMV.

22. A method of altering the levels of a protein encoded by a target gene in a plant seed comprising:
   a) transforming a plant with binary transgenic viral expression system comprising:
      1) a heritable, chromosomally-integrated proreplicon lacking a functional replication gene for autonomous episomal replication, and comprising:
         i) cis-acting viral elements required for viral replication;
         ii) a target gene comprising at least one suitable regulatory sequence; and
         iii) flanking sequences that enable the excision of the elements of i) and ii); and
      2) a heritable, chromosomally-integrated chimeric trans-acting replication gene comprising a seed specific promoter operably-linked to a viral replication protein coding sequence, wherein said cis-acting viral elements and said viral replication protein coding sequence are derived from the same virus; and
   b) growing the transformed plant under conditions wherein the protein is expressed in the plant seed.

* * * * *

SEQUENCE LISTING

<160> NUMBER OF SEQ ID NOS: 14

<210> SEQ ID NO 1
<211> LENGTH: 35
<212> TYPE: DNA
<213> ORGANISM: Unknown
<220> FEATURE:
<223> OTHER INFORMATION: Description of Unknown Organism:primers

<400> SEQUENCE: 1
cgtccggatc caattctccc catacaagag tatct                35

<210> SEQ ID NO 2
<211> LENGTH: 35
<212> TYPE: DNA
<213> ORGANISM: Unknown
<220> FEATURE:
<223> OTHER INFORMATION: Description of Unknown Organism:primers

<400> SEQUENCE: 2
gtcgacccat ggttaaagat ccacgaaacg catgt                35

<210> SEQ ID NO 3
<211> LENGTH: 41
<212> TYPE: DNA
<213> ORGANISM: Unknown
<220> FEATURE:
<223> OTHER INFORMATION: Description of Unknown Organism:primers

<400> SEQUENCE: 3
gctgcggccg ctccaaaagt tatatgaatt ggtagtaagg t                41

<210> SEQ ID NO 4
<211> LENGTH: 27
<212> TYPE: DNA
<213> ORGANISM: Unknown
<220> FEATURE:
<223> OTHER INFORMATION: Description of Unknown Organism:primers

<400> SEQUENCE: 4
cgagtcgacg cgcggccatc cggtaat                27

<210> SEQ ID NO 5
<211> LENGTH: 29
<212> TYPE: DNA
<213> ORGANISM: Unknown
<220> FEATURE:
<223> OTHER INFORMATION: Description of Unknown Organism:primers

<400> SEQUENCE: 5
gcaggatcca ctggattttg gttttagga                29

<210> SEQ ID NO 6

```
<211> LENGTH: 31
<212> TYPE: DNA
<213> ORGANISM: Unknown
<220> FEATURE:
<223> OTHER INFORMATION: Description of Unknown Organism:primers

<400> SEQUENCE: 6
gcatctagaa aatcaccagt ctctctctac a                               31

<210> SEQ ID NO 7
<211> LENGTH: 29
<212> TYPE: DNA
<213> ORGANISM: Unknown
<220> FEATURE:
<223> OTHER INFORMATION: Description of Unknown Organism:primers

<400> SEQUENCE: 7
gctgcggccg ctggagtaaa gaaggagtg                                  29

<210> SEQ ID NO 8
<211> LENGTH: 28
<212> TYPE: DNA
<213> ORGANISM: Unknown
<220> FEATURE:
<223> OTHER INFORMATION: Description of Unknown Organism:primers

<400> SEQUENCE: 8
gccagatcta gtaacataga tgacaccg                                   28

<210> SEQ ID NO 9
<211> LENGTH: 38
<212> TYPE: DNA
<213> ORGANISM: Unknown
<220> FEATURE:
<223> OTHER INFORMATION: Description of Unknown Organism:primers

<400> SEQUENCE: 9
cgtgagctct ccaaaagtta tatgaattgg tagtaagg                        38

<210> SEQ ID NO 10
<211> LENGTH: 35
<212> TYPE: DNA
<213> ORGANISM: Unknown
<220> FEATURE:
<223> OTHER INFORMATION: Description of Unknown Organism:primers

<400> SEQUENCE: 10
cctcgagcca tggtttgaat taaagatcca cgaaa                           35

<210> SEQ ID NO 11
<211> LENGTH: 44
<212> TYPE: DNA
<213> ORGANISM: Unknown
<220> FEATURE:
<223> OTHER INFORMATION: Description of Unknown Organism:primers

<400> SEQUENCE: 11
cgtgagctct ccaaaagtta tatgaattgg tagtaaggta aggt                 44

<210> SEQ ID NO 12
<211> LENGTH: 27
<212> TYPE: DNA
<213> ORGANISM: Unknown
<220> FEATURE:
<223> OTHER INFORMATION: Description of Unknown Organism:primers

<400> SEQUENCE: 12
```

```
ggtagatctg cgcggccatc cggtaat                                           27

<210> SEQ ID NO 13
<211> LENGTH: 22
<212> TYPE: DNA
<213> ORGANISM: Unknown
<220> FEATURE:
<223> OTHER INFORMATION: Description of Unknown Organism:primers

<400> SEQUENCE: 13
cacggatcca gatcgccgcg tc                                                22

<210> SEQ ID NO 14
<211> LENGTH: 34
<212> TYPE: DNA
<213> ORGANISM: Unknown
<220> FEATURE:
<223> OTHER INFORMATION: Description of Unknown Organism:primers

<400> SEQUENCE: 14
cctcgagcca tggactctgg atggatggat gatg                                   34
```